(12) United States Patent  
Koeth

(10) Patent No.: US 9,707,010 B2  
(45) Date of Patent: Jul. 18, 2017

(54) INSUFFLATION TUBE COMPRISING A HUMIDIFYING MATERIAL AND A HEATING ELEMENT, FOR LAPAROSCOPY

(71) Applicant: W.O.M. WORLD OF MEDICINE GMBH, Berlin (DE)

(72) Inventor: Yves Koeth, Berlin (DE)

(73) Assignee: W.O.M. World of Medicine GmbH, Berlin (DE)

( * ) Notice: Subject to any disclaimer, the term of this patent is extended or adjusted under 35 U.S.C. 154(b) by 130 days.

(21) Appl. No.: 14/409,887

(22) PCT Filed: Jan. 15, 2014

(86) PCT No.: PCT/DE2014/000017  
§ 371 (c)(1),  
(2) Date: Dec. 19, 2014

(87) PCT Pub. No.: WO2014/111083  
PCT Pub. Date: Jul. 24, 2014

(65) Prior Publication Data  
US 2015/0196323 A1    Jul. 16, 2015

(30) Foreign Application Priority Data

Jan. 15, 2013  (DE) .................. 10 2013 000 492  
Jun. 18, 2013  (DE) .................. 10 2013 010 097

(51) Int. Cl.
| | |
|---|---|
| A61B 17/34 | (2006.01) |
| A61M 16/16 | (2006.01) |
| A61B 1/313 | (2006.01) |
| A61M 13/00 | (2006.01) |
| A61M 16/18 | (2006.01) |

(52) U.S. Cl.  
CPC ........ *A61B 17/3474* (2013.01); *A61B 1/3132* (2013.01); *A61M 13/003* (2013.01); *A61M 16/18* (2013.01); *A61M 2202/0225* (2013.01); *A61M 2205/3368* (2013.01); *A61M 2205/3372* (2013.01); *A61M 2205/3653* (2013.01); *A61M 2210/1021* (2013.01)

(58) Field of Classification Search  
CPC .................................................. A61B 17/3474  
USPC ........................................................ 600/560  
See application file for complete search history.

(56) References Cited

U.S. PATENT DOCUMENTS

| | | | |
|---|---|---|---|
| 5,630,822 A * | 5/1997 | Hermann ......... | A61B 17/00234 606/114 |
| 6,068,609 A | 5/2000 | Ott et al. | |
| 2003/0181857 A1* | 9/2003 | Blake ................. | A61B 17/3417 604/113 |
| 2004/0102731 A1* | 5/2004 | Blackhurst ......... | A61B 1/00154 604/26 |

(Continued)

FOREIGN PATENT DOCUMENTS

| | | |
|---|---|---|
| DE | 4211986 A1 | 10/1993 |
| DE | 4331559 A1 | 6/1994 |

(Continued)

*Primary Examiner* — Michael C Stout  
*Assistant Examiner* — Nicholas E Kolderman  
(74) *Attorney, Agent, or Firm* — Mayer & Williams, PC

(57) ABSTRACT

The present invention relates to a tube with an integrated heating element for laparoscopy. By means of a humidifying material in the interior of the tube, the gas introduced during laparoscopy is heated and humidified.

18 Claims, 2 Drawing Sheets

(56) References Cited

U.S. PATENT DOCUMENTS

2004/0254524 A1* 12/2004 Spearman ........... A61M 13/003
          604/26
2010/0094200 A1*  4/2010 Dean .................... A61B 18/00
          604/26
2010/0206308 A1   8/2010 Klasek et al.

FOREIGN PATENT DOCUMENTS

| DE | 19510710      | 9/1996  |
|----|---------------|---------|
| EP | 0827417 B1    | 10/2004 |
| WO | 02/32486 A1   | 4/2002  |
| WO | 2008/095245 A1| 8/2008  |
| WO | 2011/078701 A1| 6/2011  |
| WO | 2013/137753 A1| 9/2013  |

* cited by examiner

INSUFFLATION TUBE COMPRISING A HUMIDIFYING MATERIAL AND A HEATING ELEMENT, FOR LAPAROSCOPY

BACKGROUND OF THE INVENTION

The present invention relates to a tube with an integrated heating element for laparoscopy. By means of a humidifying material in the interior of the tube the gas introduced during laparoscopy is heated and humidified. The present patent application claims the priorities of the previous German applications DE 102013000492.6 (date of filing: 15 Jan. 2013) and DE 1020130100967.6 (date of filing: 18 Jun. 2013).

Laparoscopy is a medical intervention by means of which the abdominal cavity and the organs therein can be visually examined. For this purpose, small skin incisions (0.3-2 cm) in the abdominal wall are typically made, and a trocar is introduced therethrough, which in turn can accommodate an optical device. With the aid of a special endoscope (laparoscope), the abdomen can be examined. In diagnostic laparoscopy, the abdomen is only visually inspected, and in a therapeutic process, operative interventions can also be performed.

Typically, at the beginning of the laparoscopy, the abdomen is filled with gas, in order to create a pneumoperitoneum. For this purpose, various gases have already been used, such as air, nitrogen or carbon dioxide ($CO_2$). The use of carbon dioxide gas has proven particularly successful. It was found that it is reasonable, in particular with longer laparoscopic interventions, on the one hand to heat the introduced gas and on the other hand to humidify it. The gas heating is intended so that the patient is not cooled down, and to avoid a diffuse feeling of pain in the patient, which probably is a consequence of a local cooling upon the entry of cold gas. The humidification serves for preventing drying out the inner abdominal surfaces, in order to avoid the cooling occurring thereby. It is important herein to achieve a relative gas humidity of more than 90% during the laparoscopy. When employing this in laparoscopy, the peculiarity results that the volume flows will strongly vary. An average gas flow of 1-3 l/min. can be assumed. If there should be, however, a larger leakage, for instance by activation of a ventilation, then immediately gas flow rates >20 l/min. are required, and these, too, should achieve the required humidity level of more than 90%.

For this purpose, the prior art provides suggestions. For instance, the German patent specification DE 19510710 describes a device that provides a means for adjusting the gas humidity (for instance a sponge) and which optionally may include an additional heating element.

U.S. Pat. No. 6,068,609 discloses an alternative device with a chamber that on the one hand comprises a sponge material, on the other hand provides a resistor heating. The humidification chamber includes a Luer lock port, which permits water to be filled into the chamber. The chamber of U.S. Pat. No. 6,068,609 is brought by corresponding ports into the gas flow of the insufflation device. Further prior art includes documents EP 0827417B1, US 2010/0206308 A1, DE 4331559 A1, and DE 4211986 A1.

The devices known from the prior art have technical drawbacks.

On the one hand, the chamber disposed at patient's side prevents the operability of the insufflation tube during the operative intervention. Due to the size and the weight of the chamber, it may be disturbing in the near operational field to the doctor in charge.

Further, the humidification rates of the gas for different flow rates cannot be kept at uniformly high levels. In particular, the short way of the gas through the chamber prevents an optimum humidification at high flow rates.

In order to increase the humidification capacity, the gas is conducted in the above solutions through a material (for instance a sponge). Thereby, the counter-pressure of the tube is substantially increased, and the maximum flow capacity is decreased. This has considerable disadvantages when maintaining the pneumoperitoneum. In particular, if high refill rates are required (for instance when using suction pumps), the insufflation capacity may under certain conditions not be sufficient, and the pressure in the abdominal cavity may possibly not be maintained.

Further, the introduction of the additional chamber for the humidification of the gas is disadvantageous for the production cost of the insufflation tube. The additionally required parts will substantially increase the cost.

SUMMARY OF THE INVENTION

It is therefore the object of the present invention to provide an improved device for heating and humidifying insufflation gases, which does not exhibit the mentioned drawbacks.

BRIEF DESCRIPTION OF THE DRAWINGS

FIGS. 2a-2d show how such tube is built up. FIG. 2a shows a tube which has a multiplicity of openings over its length. The opposite end of the tube is closed. Upon gas supply (1) the gas exits the tube via the openings in radial direction (2).

Figure 1:
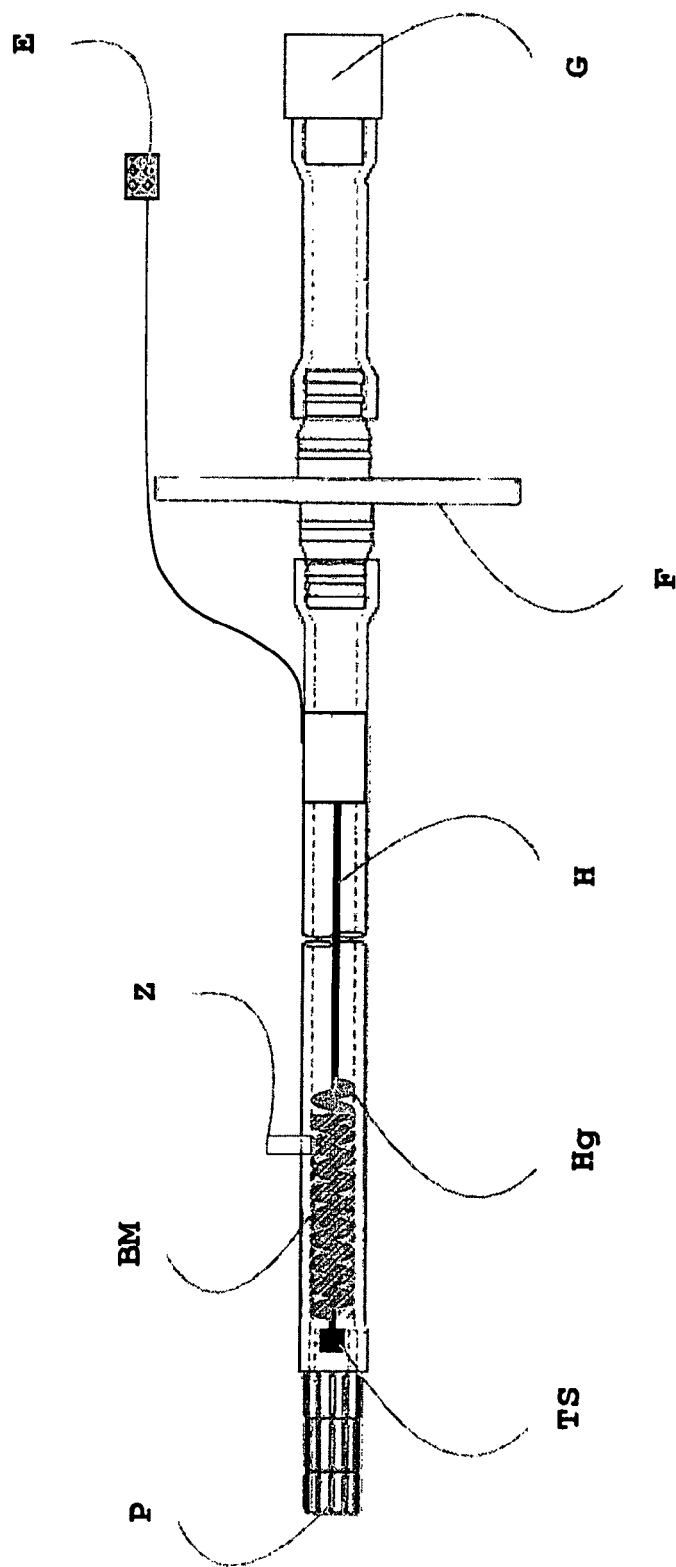
FIG. 1 shows an exemplary embodiment as outlined in example 1. The insufflation tube according to the invention has a gas supply (G) and a filter (F). Inside the tube there is a helical heating element (Hg) which is heated by electrical power supplied by the electrical connector (E). The heating element is wrapped with sterile gauze bandage as humidifying material (BM). The tube contains a water delivery port (Z). At the patient sided end of the tube (P) is a temperature sensor (TS) located.

The device described in FIG. 2a is helically covered with the heating wire (3) as shown in FIG. 2b.

The device shown in FIG. 2b is further wrapped with humidifying material (4) as shown in FIG. 2c.

The whole construct shown in FIG. 2c is finally introduced into a larger outer tube (7) and connected therewith so that the gas inlet (1) occurs via the inner tube only (6) as shown in FIG. 2d. The gas flowing in (1) is heated by the heating wire and humidified by means of the humidifying material and then flows out (5) from the end of the outer tube (7).

DETAILED DESCRIPTION OF THE INVENTION

This object is achieved by the subject matter of the patent claims, i.e. an insufflation tube with an integrated heating and humidifying device. The tube according to the invention includes a heating element, which for instance in the form of a resistor heating can heat the insufflation gas (for instance $CO_2$).

The heating power of the heating system must be adjustable, since, depending on the actual humidification rate, very different amounts of energy are required for heating the gas. The tube according to the invention may provide a temperature probe that is preferably positioned at the patient-side end of the tube. By the probe it can be assured that the air flowing through the tube does not exceed a temperature of 37° C. on the exit side.

Typically, a heating wire is provided in the insufflation tube for heating. The wire may loosely be placed in the interior of the tube, it may however also be attached at one or a plurality of points on the tube wall. For increasing its power, the heating wire may be provided in the form of a helix in the interior of the tube. The thus obtained extension of the heating wire leads to an increase of the surface and thus, with the same resistor or an adjusted voltage, to an increase of the heating power.

Alternatively, the heating wire may also be arranged outside of the tube. Furthermore, it may for instance be cast into the tube wall.

The tube may be made from any material, which is commonly used in the medical field, for instance PVC, PUR, TPU, or silicone. Tube diameters being typical in this field are 6-14 mm.

The heating wire may be made of any conductive materials, in particular metals and metal alloys, e.g. iron, nickel, chrome, or copper. The diameter of the wire is for instance 0.25-1 mm. Preferred is a wire in the form of a helix with a diameter of 3-4 mm. For typical use, the wire has a length of 50 cm-10 m. When a voltage of 5-25 V is applied, thus a heating power of 5-50 W can be achieved. Preferably, the heating wire has an electrical insulation, so to avoid short-circuits. If the heating wire is integrated in the tube wall or is arranged outside of the tube, of course higher heating powers will be required, than if the heating wire were located in the interior of the tube.

In the immediate vicinity of the heating element, in the interior of the tube, further a humidifying material is positioned. It is a porous material which is capable of absorbing a liquid, in particular water. This humidifying material may for instance enclose the heating element, so that the heating element has essentially over its total length a direct contact with the humidifying material. In an alternative embodiment, wherein the heating wire is integrated in the tube wall or is even arranged outside of the tube, the humidifying material is positioned immediately at the inner tube wall, so that essentially a full face contact of the heated tube wall with the humidifying material is obtained. As a humidifying material can in the simplest case (sterilized) cotton be used that is capable of absorbing a certain amount of water. Alternatively, the following materials can be used: sponges, superabsorbent polymers (SAP), blotting paper, phenolic resin materials. Further materials are imaginable.

The arrangement of the humidifying material may be over the complete length of the tube of for instance 1-4 meters (preferred length 2.5-3.5 m). Alternatively, the material may also be arranged over a shorter distance (for instance only 40-60 cm) in the tube. In the latter case, it is important to pay attention to that the tube portion with the heating and humidifying device is preferably positioned at the patient-side end of the tube. As experience teaches, the tube portion with the heating and humidifying device should occupy at least 40 cm in length and at least 15% of the total tube length.

The larger the distance of the humidifying material to the tube, the less counter-pressure is produced by the tube during insufflation. The distance may also be substantially reduced. Thereby, depending on the type of the used material, the counter-pressure will increase. The man skilled in the art can in a simple way vary the individual parameters, in order to achieve a favorable embodiment. For safety reasons, there will always be the wish to limit the pressure in the tube. In order to obtain the desired gas flow of up to 50 l/min, with a desired relative gas humidity of more than 90%, the man skilled in the art will select the materials and distances such that a pressure of <50 mm Hg, preferably <20 mm Hg is sufficient.

In a possible embodiment of the invention, a cotton fabric is wrapped in the form of a helix over the complete length of the helix around the heating wire.

The water absorption capacity of the porous material depends of course on the respective material. For normal operation, approx. 200 liters gas are needed. In order to humidify it to nearly 100% of relative humidity, ~10 ml liquid are required. It is advantageous, when the amount of the used humidifying material can absorb this amount of liquid.

Depending on the intended duration of the laparoscopic intervention and on the gas flow, it may be sufficient to humidify the porous material once before the laparoscopy. In particular, with longer lasting operations, another humidification may be necessary. For this purpose, the tube may provide an optional delivery port, which permits further introduction of water. For the man skilled in the art it is self-evident that water used before the operation as well as during the operation, if applicable, must be sterile.

In an alternative embodiment of the invention, the heating element may also be configured such that a resistance change of the heating element occurs with heating. By measurement of the resistance, in this case, the temperature of the heating element can be determined. Thereby, the introduction of an additional temperature probe may possibly be avoided.

The tube according to the invention has the advantage that except for the humidifying material, no additional components and no matching ports for this purpose are required, so that the tube can be produced as a single piece. Thus, the tube can be produced in a more economical way than for the solutions mentioned in prior art.

Further, in comparison to a standard heated insufflation tube, there is no difference in the operability for the doctor in charge during the operative intervention.

Due to the low counter-pressure that the tube generates, high flow rates of 40-50 l/min and more can be obtained.

Due to the longer residence time of the gas at the humidifying device, a high humidification rate (more than 90% of rel. gas humidity) can be achieved even with the high flow rates.

The tube may be made of the conventional plastic materials used in the medical field, such as for instance silicone, TPU, PUR, or PVC.

In another alternative embodiment, the insufflation tube has in its interior another tube, through which the insufflation gas is introduced into the insufflation tube. This inner tube is gas-permeable, so that the gas passage is secured. This may for instance take place by that the tube has on its outer surface a multiplicity of openings, so that the insufflation gas can flow out in a radial direction. For this purpose, for example so-called braided tubes can be used that are available in the most different embodiments. Typical materials for this inner tube are the ones mentioned above, preferably silicone, TPU, PUR, or PVC, with a wire mesh also being imaginable. In this embodiment, the humidifying material and the heating element are wrapped around the inner tube with the radial exit openings. This may for instance be achieved such that first a helix-shaped nickel-chrome wire is wound around the tube, and then the humidifying material covers the heating element. In an alternative embodiment, first a layer of humidifying material serves to cover the inner tube. Around this humidifying material, then the heating element is wound in a helical shape. Optionally, in this embodiment, a second layer of humidifying material may form another cover. It is common to all these embodiments, that over the complete length of the inner tube the insufflation gas mainly flows out in a radial direction and in this process is heated as well as humidified. Due to the better humidity absorption of a warmer gas, it is preferred that first heating and then humidifying takes place.

EXAMPLES

The present invention is explained in more detail by the following examples, without this being intended to be limiting.

Example 1

In a tube of PVC, which has a length of 3 m, a helical heating element is positioned over a distance of 90 cm. The heating element consists of nickel-chrome. The heating element is supplied with power via electrical leads to electrical connection E. By means of a voltage of 24 V, an electrical heating power of ~30 watts is achieved.

A sterile gauze bandage as a humidifying material BM is wound around the heating element Hg, so that the heating element has essentially everywhere immediate contact with the humidifying material. It is the following material: cotton 68%, polyamide 24%, elastane 8%. In addition, a temperature probe TS is provided at the exit of the tube (see FIG. 1).

Before starting the laparoscopy, the porous material is humidified with ~10 ml sterile water. Feeding the water is achieved via the additional access/via the patient-side end of the tube. The tube is provided at its patient-side end P with a Veress needle that is introduced into the abdomen of the patient. Before the introduction, it is secured, by the temperature probe TS present in the tube, that the gas temperature at the exit is not higher than 37° C. Via the tube, a gas flow of up to 50 l/min can be fed to the patient, but this gas flow can significantly be reduced when using suitable instruments, for instance a Veress cannula. The gas flow from gas inlet G first passes filter F before arriving at the heated part of the tube.

The laparoscopic intervention using the tube according to the invention may last up to 60 min., and after every 200 liters gas consumption approx. 10 ml water are refilled via the delivery port Z.

Example 2

A nickel-chrome wire is wrapped around a braided tube with a length of 50 cm made of the material PET (diameter 3 mm) that has a multiplicity of openings (<0.5 mm) over the complete length. Over the nickel-chrome wire, a layer of a sterile cotton fabric is applied. The covered tube formed in this way is introduced into a PVC tube of 3 m length (diameter 10 mm) The heating element is supplied with power via electrical leads. By means of a voltage of 24 volts, an electrical heating power of approx. 50 watts is achieved. The above humidifying material further contains, in addition to cotton, polyamide and elastane (see Example 1). Furthermore, a temperature probe is provided at the exit of the tube.

Figure 2:
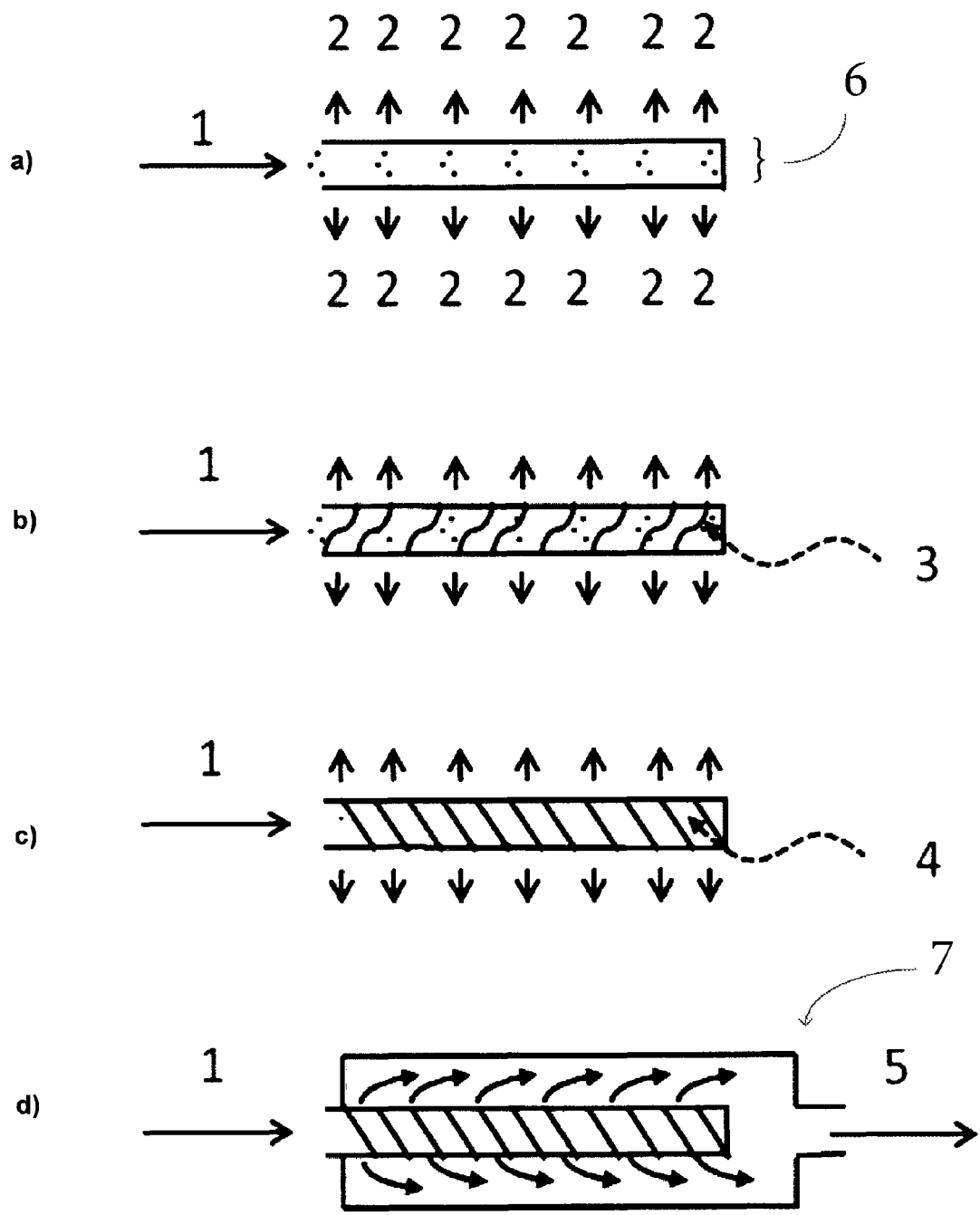
FIG. 2 shows an exemplary embodiment as provided in example 2.

The gas supply takes exclusively place via the inner tube. Such an insufflation tube according to Example 2 is shown in FIG. 2. FIG. 2a shows such a tube that has a multiplicity of openings on the outer surface. The gas supply (1) is shown on the left-hand side of the figure. The opposite end of the tube is closed, so that the gas exit occurs via the multiplicity of openings in a radial direction (2). FIG. 2b shows the helical cover of the tube with the heating wire (3). FIG. 2c shows the further wrapping with the humidifying material (4). The construct illustrated in FIG. 2c is introduced into a larger tube and connected therewith, so that the gas inlet occurs via the inner tube only (1). The gas flowing in is heated by the heating wire and humidified by means of the humidifying material and then flows off from the end of the outer tube (5).

Before starting the laparoscopy, the humidifying material is humidified with approx. 10 ml of sterile water. Feeding the water is achieved via an additional access or via the patient-side end of the tube. The tube is provided at its patient-side end with a Veress needle that is introduced into the abdomen of the patient. Before the introduction, it is secured, by the temperature probe present in the tube, that the gas temperature at the exit is not higher than 37° C. Via the tube, a gas flow of up to 40 l/min is fed to the patient, with the pressure in the inner tube not exceeding 30 mm Hg. The laparoscopic intervention using the tube according to the invention may last up to 60 min., and after every 200 liters gas consumption approx. 10 ml water are refilled via the delivery port.

LIST OF REFERENCES OF FIG. 1

P to the patient
BM humidifying material
Z delivery port
E electrical connection
TS temperature probe
Hg heating wire helix
H heating wire
F filter
G to the gas supply device

The invention claimed is:

1. An insufflation device for use in laparoscopy, comprising:
   a tube having an interior and an exterior;
   a heating element positioned within the interior of said tube; and
   a humidifying material positioned in a surrounding area of said heating element,
   wherein the interior of the tube has an inner tube through which an insufflation gas is introduced into the inner tube wherein the inner tube is gas-permeable and wherein the inner tube comprises a multiplicity of openings on at least one outer surface of the inner tube such that the insufflation gas flows out in a radial direction and wherein the inner tube is wrapped with the humidifying material and the heating element;
   wherein total tube length is 1-4 m, and
   wherein the heating element and the humidifying material occupy at least 40 cm in length of the tube and at least 15% of the total tube length.

2. The insufflation device according to claim 1, further comprising a temperature probe, wherein the temperature probe controls power of the heating element.

3. The insufflation device according to claim 1, wherein the heating element includes a temperature-dependent resistor that permits a temperature measurement during insufflation.

4. The insufflation device according to claim 2 wherein the tube is configured to allow a separate access to pre- and intra-operative humidification of the humidifying material.

5. The insufflation device according to claim 1, wherein the heating element comprises a wire helix.

6. The insufflation device according to claim 1, wherein the humidifying material comprises a sterilized cotton fabric.

7. The insufflation device according to claim 1, wherein the tube comprises PVC, PUR, TPU, or silicone.

8. The insufflation device according to claim 1, wherein the inner tube is made of a braided tube.

9. The insufflation device according to claim 1, further comprising a gas inlet, to which a gas supply may be provided.

10. The insufflation device according to claim 9, wherein the inner tube made of a braided tube is closed at an end of the inner tube opposite the gas inlet.

11. The insufflation device according to claim 9, wherein gas flow at the gas inlet passes a filter prior to reaching the heating element.

12. An insufflation device for use in laparoscopy, comprising:
a tube having an interior and an exterior;
a heating element positioned within the interior of said tube; and
a humidifying material positioned in a surrounding area of said heating element, wherein said humidifying material is wrapped around said heating element;
wherein the interior of the tube has an inner tube through which an insufflation gas is introduced into the inner tube wherein the inner tube is gas-permeable and wherein the inner tube comprises a multiplicity of openings on at least one outer surface of the inner tube such that the insufflation gas flows out in a radial direction and wherein the inner tube is wrapped with the humidifying material and the heating element;
wherein the insufflation gas introduced into said tube is heated by said heating element and humidified by said humidifying material inside said tube.

13. The insufflation device according to claim 12, wherein total tube length is 1-4 m, and wherein the heating element and the humidifying material occupy at least 40 cm in length of the tube and at least 15% of the total tube length.

14. The insufflation device according to claim 12, further comprising a temperature probe, wherein the temperature probe controls power of the heating element.

15. The insufflation device according to claim 12, wherein the heating element includes a temperature-dependent resistor that permits a temperature measurement during insufflation.

16. The insufflation device according to claim 12 wherein the tube is configured to allow a separate access to pre- and intra-operative humidification of the humidifying material.

17. The insufflation device according to claim 12, wherein the humidifying material comprises a sterilized cotton fabric.

18. The insufflation device according to claim 12, further comprising a gas inlet, to which a gas supply may be provided, wherein the inner tube made of a braided tube is closed at its end opposite the gas inlet and wherein gas flow at the gas inlet passes a filter prior to reaching the heating element.

* * * * *